(12) United States Patent
Kawata

(10) Patent No.: US 6,748,099 B1
(45) Date of Patent: Jun. 8, 2004

(54) COMPUTER-AIDED IMAGE DIAGNOSIS SYSTEM

(75) Inventor: Masayuki Kawata, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 413 days.

(21) Appl. No.: 09/589,071

(22) Filed: Jun. 8, 2000

(30) Foreign Application Priority Data

Jun. 8, 1999 (JP) ............................................ 11/161597

(51) Int. Cl.[7] .................................................. G06K 9/00
(52) U.S. Cl. ......................................... 382/132; 378/37
(58) Field of Search ................................ 382/128, 131, 382/132, 309, 310, 311; 378/37; 128/922; 600/407

(56) References Cited

U.S. PATENT DOCUMENTS

| | | | |
|---|---|---|---|
| 5,235,510 A | * 8/1993 | Yamada et al. | ............. 600/300 |
| 5,761,334 A | 6/1998 | Nakajima et al. | ............ 382/132 |
| 5,982,917 A | * 11/1999 | Clarke et al. | ................ 382/132 |
| 6,456,403 B1 | * 9/2002 | Archer et al. | ................ 358/474 |

* cited by examiner

*Primary Examiner*—Leo Boudreau
*Assistant Examiner*—Ryan J. Miller
(74) *Attorney, Agent, or Firm*—Sughrue Mion, PLLC

(57) ABSTRACT

A computer-aided image diagnosis system having (1) a detection section for detecting an abnormal shadow candidate in a radiation image, based on image information representing the radiation image, (2) a switching section for switching a destination where a diagnostic image is output, in accordance with a result of the detection of the abnormal shadow candidate, and (3) an outputting section for outputting the diagnostic image which corresponds to the detection result.

7 Claims, 1 Drawing Sheet

COMPUTER-AIDED IMAGE DIAGNOSIS SYSTEM

BACKGROUND OF THE INVENTION

1. Field of the Invention

The present invention relates to an improvement in a computer-aided image diagnosis system that detects an abnormal shadow candidate in a radiation image, based on image information representing the radiation image.

2. Description of the Related Art

In the medical field, a wide variety of image-forming modalities (image input units), such as computed tomography (CT), computed radiography (CR) and the like, have spread as units that generate an image for diagnosis.

In addition, computer-aided image diagnosis systems have been proposed in which, based on image information representing a diagnostic radiation image acquired by the image-forming modality, an abnormal shadow candidate appearing in the radiation image is automatically detected by a computer, and the image, etc., of the detected abnormal shadow candidate are displayed on a display unit or recorded on a storage medium such as film (Japanese Unexamined Patent Publication Nos. 8(1996)-294479 and 8(1996)-287230).

The words "abnormal shadow" mean a shadow appearing in a radiation image because of an abnormal part or the like on which a cancer has grown or is growing. For example, in a mammogram (which is a radiation image of the breast obtained by mammography), the intumescence shadow or micro-calcification shadow corresponds to the abnormal shadow.

For instance, for a mammogram, the computer-aided image diagnosis system represents a density gradient (or a brightness gradient) in an image as a density gradient vector, and detects an image portion where the degree of concentration of the density gradient vector is high, as the intumescence shadow candidate, using an iris filer. Also, with a morphologic algorithm employing multiplex elements in accordance with the size of a micro-calcification shadow to be detected, an image portion whose density varies in a range spatially narrower than the multiplex elements is detected as the micro-calcification shadow.

In the case where the abnormal shadow candidate is detected in this manner, it is output (e.g., displayed) as a diagnostic image in various forms, along with or separately from the entire radiation image (Japanese Unexamined Patent Publication No. 8(1996)-294479, etc.).

The computer-aided image diagnosis system, incidentally, must handle an image of very high quality for the process of detecting the aforementioned abnormal shadow candidate and to observe the detected abnormal shadow candidate in detail. That is, since the image information representing a radiation image has a large number of pixels and high gradation (number of bits), the data size is much larger. Also, a display unit to display a diagnostic image has to have high resolution to express a high-quality image, and furthermore, a large-capacity storage medium is employed to store image information.

In the conventional computer-aided image diagnosis system, in order to observe and read uniformly in detail a large-data-size diagnostic image whether an abnormal shadow candidate is detected or not, the diagnostic image is output in various display forms to a high-quality display unit having high resolution and high gradation and is stored in a storage medium.

However, since the diagnostic image is large in data size, as described above, displaying the diagnostic image on the aforementioned display unit much higher in display quality results in slow output response and becomes a problem particularly in the case where a great number of diagnostic images are handled within a limited time, like a group examination. In addition, if all diagnostic images are stored uniformly in large data size in a storage medium, the time required for the storing operation will become longer and there will be a problem that the amount of storage medium used up increases.

SUMMARY OF THE INVENTION

The present invention has been made in view of the aforementioned problems. Accordingly, it is an object of the present invention to provide a computer-aided image diagnosis system that is capable of performing proper output for each diagnostic image to be observed and read. Another object of the invention is to provide a computer-aided image diagnosis system which is capable of performing proper storage for each diagnostic image to be observed and read.

To achieve the aforementioned objects and in accordance with one important aspect of the present invention, there is provided a first computer-aided image diagnosis system which switches a destination where a diagnostic image is output, in accordance with the result of detection of an abnormal shadow candidate.

The first computer-aided image diagnosis system comprises: means for detecting an abnormal shadow candidate in a radiation image, based on image information representing the radiation image; means for switching a destination where a diagnostic image is output, in accordance with a result of the detection of the abnormal shadow candidate; and means for outputting the diagnostic image which corresponds to the detection result.

The process of detecting an abnormal shadow candidate in a radiation image, based on image information representing the radiation image, can employ, for example, the process of detecting an intumescence shadow candidate by employing an iris filer or the process of detecting a micro-calcification shadow candidate by a morphologic algorithm, disclosed in the aforementioned Japanese Unexamined Patent Publication Nos. 8(1996)-294479 and 8(1996)-287230.

The words "diagnostic image which corresponds to the result of detection of an abnormal shadow candidate" mean various images, such as an original radiation image, an image obtained by performing a marking process or an emphasizing process, etc., on an abnormal shadow candidate detected from an original radiation image, an image obtained by extracting a detected abnormal shadow candidate alone, an image disposed so that an original image and an abnormal shadow candidate extracted from the original image can be output to a single display screen or storage medium, and so on.

The aforementioned "destination where a diagnostic image is output" refers to a plurality of display units differing from one another in display quality, or these display units provided with a storage unit which stores the aforementioned diagnostic image on a predetermined storage medium. Therefore, in accordance with the result of detection of an abnormal shadow candidate, the switching means is capable of switching one of the plurality of display units which displays the diagnostic image. The switching means is also capable of switching one of the plurality of display units which displays the diagnostic image and switching whether or not the diagnostic image is stored on a predetermined storage medium.

The words "display quality" refer to image quality, such as resolution, gradation and the like, speed required for displaying, etc.

The expression "switch in accordance with the result of detection of an abnormal shadow candidate" means switching according to whether or not an abnormal shadow candidate has been detected, i.e., whether the number of abnormal shadow candidates is 1 or more, or 0. Also, switching may be performed according to the number of abnormal shadow candidates detected. Furthermore, the switching may be three or more switchings as well as two switchings.

In accordance with another important aspect of the present invention, there is provided a second computer-aided image diagnosis system which switches the data storage size of a diagnostic image in accordance with the result of detection of an abnormal shadow candidate.

The second computer-aided image diagnosis system comprises: means for detecting an abnormal shadow candidate in a radiation image, based on image information representing the radiation image; means for switching the data size of the diagnostic image to be stored as the diagnostic image, in accordance with a result of the detection of the abnormal shadow candidate; and means for storing the diagnostic image which corresponds to the detection result.

The words "switch data size" mean that data size is switched, for example, by varying the compression size of data. In addition, data size after compression may be switched indirectly by switching a method of compression, such as reversible compression, irreversible compression and the like.

According to the first computer-aided image diagnosis system of the present invention, a destination where a diagnostic image is output can be switched according to the result of detection of an abnormal shadow candidate. Therefore, proper output can be performed for each diagnostic image that is to be observed and read. More specifically, for example, a diagnostic image for a radiation image, from which an abnormal shadow candidate was detected, is output to a high-quality display unit to observe and read the existence of the abnormal shadow candidate in detail, as before. On the other hand, a diagnostic image for a radiation image, from which no abnormal shadow candidate was detected, is output to a display unit relatively inferior in display quality to the aforementioned high-quality display unit to recognize and read the nonexistence of an abnormal shadow candidate in a simple manner. In this way, the demand for a diagnostic image that is to be observed and read in detail is compatible with the demand for a quick output response.

According to the second computer-aided image diagnosis system of the present invention, the data size of a diagnostic image to be stored can be switched in accordance with the result of detection of the abnormal shadow candidate. Each diagnostic image, which is to be observed and read, can be stored in an appropriate data size. More specifically, for instance, a diagnostic image for a radiation image, from which an abnormal shadow candidate was detected, is stored in data size as before, or in a reversibly compressed data size, and afterwards, the stored data can be read out to observe and read the existence of the abnormal shadow candidate in detail. On the other hand, a diagnostic image for a radiation image, from which no abnormal shadow candidate was detected, is stored in data size smaller than before, or in irreversibly compressed data size. In this way, the demand for higher reproducibility of diagnostic image data, which is to be observed and read, is compatible with the demand for a quick input-output response of storage and less consumption of a storage medium.

BRIEF DESCRIPTION OF THE DRAWINGS

The present invention will be described in further detail with reference to the accompanying drawing wherein.

DESCRIPTION OF THE PREFERRED EMBODIMENT

Figure 1:
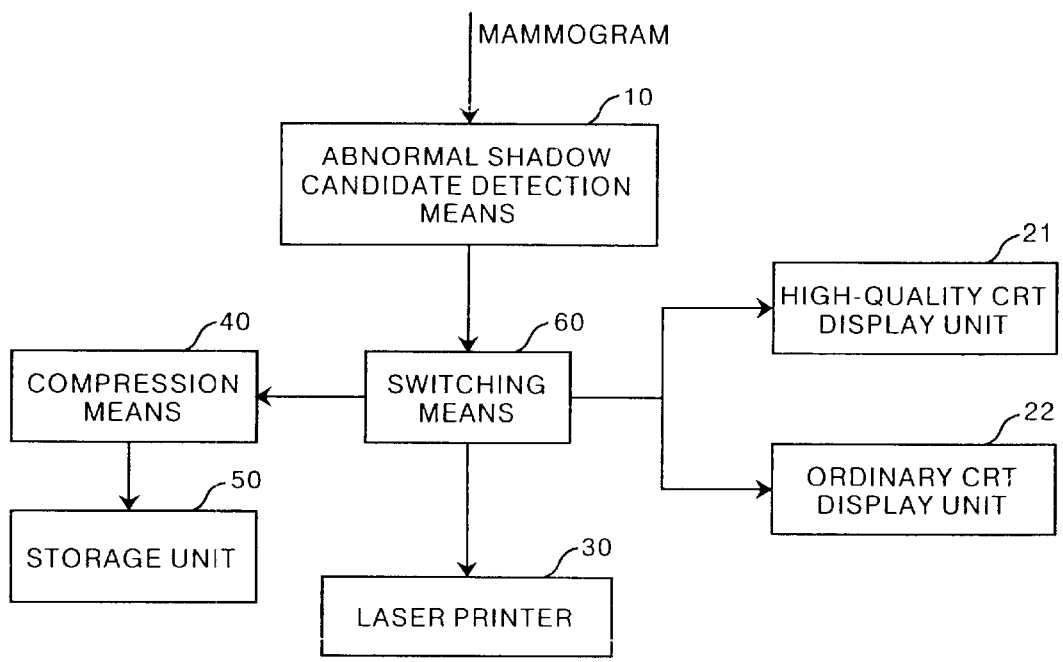
FIG. 1 is a block diagram showing an embodiment of a computer-aided image diagnosis system into which first and second computer-aided image diagnosis systems of the present invention are combined.

A preferred embodiment of the computer-aided image diagnosis system of the present invention will hereinafter be described with reference to FIG. 1. The computer-aided image diagnosis system comprises (1) abnormal shadow candidate detection means 10 which, based on input image information representing a radiation image, detects an abnormal shadow candidate in the radiation image and generates a diagnostic image, (2) a high-quality cathode-ray-tube (CRT) display unit 21 of high resolution capable of displaying an image of high density and high gradation, (3) an ordinary CRT display unit 22 lower in resolution than the high-quality CRT display unit 21, (4) a laser printer 30 which records and outputs the diagnostic image to negative film that is used for observation and reading, (5) compression means 40 capable of switching the reversible compression or irreversible compression of the input image data, (6) a storage unit 50 which stores the image data compressed by the compression means 40 on a storage medium, and (7) switching means 60 which, in accordance with the result of detection of the abnormal shadow candidate obtained by the abnormal shadow detection means 10, switches the high-quality CRT display unit 21 or ordinarily CRT display unit 22 which displays the diagnostic image generated by the abnormal shadow detection means 10, also switches the existence of the output of the laser printer 30, and furthermore, switches the reversible compression or irreversible compression which is performed by the compression means 40.

The switching operation that is performed by the switching means 60 will be described.

When the abnormal shadow candidate detection means 10 detects even one abnormal shadow candidate, the switching means 60 performs a switching operation so that the high-quality CRT display unit 21 displays the diagnostic image generated by the abnormal shadow candidate detection means 10, also the laser printer 30 outputs the diagnostic image, and furthermore, the compression means 40 performs reversible compression.

On other hand, when the abnormal shadow candidate detection means 10 detects no abnormal shadow candidate, the switching means 60 performs switching operation so that the normal CRT display unit 22 displays the diagnostic image generated by the abnormal shadow candidate detection means 10 (original radiation image itself), also the laser printer 30 does not output the diagnostic image, and furthermore, the compression means 40 performs irreversible compression which has a higher compression factor than reversible compression.

The operation of the computer-aided image diagnosis system of this embodiment will be described.

Image data representing a predetermined mammogram obtained by computed radiography, for example, is input to the abnormal shadow candidate detection means 10. This abnormal shadow candidate detection means 10 detects and processes an abnormal shadow candidate in the mammogram, based on the input image data. Here, when an abnormal shadow candidate is detected, the abnormal shadow candidate detection means 10 generates and outputs a diagnostic image in which a whole image, representing the whole of the input mammogram, and an abnormal shadow candidate image, obtained by extracting the detected abnormal shadow candidate alone, are disposed as a single image. On the other hand, when no abnormal shadow candidate is detected, the abnormal shadow candidate detection means 10 outputs only the whole image as the diagnostic image.

Next, the switching means 60 switches a destination where the input diagnostic image is output, and the compression method to be performed by the compression means 40, in accordance with the aforementioned switching operation, based on the detection result of the abnormal shadow candidate obtained by the abnormal shadow candidate detection means 10.

More specifically, when an abnormal shadow candidate is detected, the switching means 60 outputs the diagnostic image to the high-quality CRT display unit 21 and causes the display unit 21 to display the diagnostic image as a high-resolution image of high quality. The switching means 60 also outputs the diagnostic image to the laser printer 30 and makes the printer 30 record and output the diagnostic image to negative film. Furthermore, the switching means 60 switches the compression means 40 to reversible compression.

The compression means 40 performs reversible compression, in which data size is relatively large and compression factor is relatively low, on the diagnostic image and outputs the compressed diagnostic image to the storage unit 50. Then, the storage unit 50 stores the input, reversibly compressed diagnostic image of relatively large data size on the storage medium thereof.

On the other hand, when no abnormal shadow candidate is detected, the switching means 60 outputs the diagnostic image to the ordinary CRT display unit 22 and allows the display unit 22 to display the diagnostic image as an average-resolution image of average quality (lower in picture quality than high quality). The switching means 60 also switches the compression means 40 to irreversible compression. In this case, no diagnostic image is output and recorded on negative film, because no diagnostic image is output to the laser printer 30.

"The compression means 40 performs irreversible compression, which is relatively small in data size and relatively low in compression factor, on the diagnostic image and outputs the compressed diagnostic image to the storage unit 50. Then, the storage unit 50 stores the input, reversible compressed diagnostic image of relatively small data size on the storage medium thereof."

With the foregoing operation, the diagnostic image, in which an abnormal shadow candidate to be observed and read in detail was detected, is relatively slow in responsiveness but suitable for observation and reading, because it is displayed as an image of high resolution and high gradation by the high-quality CRT display unit 21. In addition, as the diagnostic image is output and semi-permanently stored on negative film, observation and reading can be carefully performed employing the diagnostic image stored on the negative film, even in the place where a display unit such as a CRT display unit has not been installed. Furthermore, since the data size is larger than the case of irreversible compression but is stored on the storage medium as data compressed in reversible compression which allows data to be expanded to the original size perfectly, the stored data can be reproduced as the diagnostic image to be observed and read in detail, by reading out the data afterwards. On the other hand, the diagnostic image with no abnormal shadow candidate, which is not required to be observed and read in detail, is displayed on the ordinary CRT display unit 22 inferior in picture quality to the high-quality CRT display unit 21 but faster in responsiveness than the high-quality CRT display unit 21. Therefore, the nonexistence of an abnormal shadow candidate can be confirmed and read in a short time by a simple method. Moreover, wasteful use of film can be avoided because no diagnostic image is output to negative film. Furthermore, since the data size cannot be decompressed perfectly to the original data size but is stored on the storage medium as data compressed in irreversible compression smaller in data size than the case of reversible compression, the input-output responsiveness can be enhanced.

Thus, according to the computer-aided image diagnosis system of this embodiment, proper output and proper storage can be performed for each diagnostic image that is to be observed and read.

While the present invention has been described with reference to the preferred embodiment thereof, the invention is not to be limited to the details given herein, but may be modified within the scope of the appended claims.

What is claimed is:

1. A computer-aided image diagnosis system comprising:

means for detecting an abnormal shadow candidate in a radiation image, based on image information representing said radiation image;

means for switching the data size of a diagnostic image to be stored as said diagnostic image, in accordance with a result of the detection of said abnormal shadow candidate; and means for storing said diagnostic image which corresponds to said detection result;

wherein said means for switching the data size of said diagnostic image comprises switching data compression algorithms for compressing data size of said diagnostic image.

2. The computer-aided image diagnosis system as set forth in claim 1, wherein said means for switching the data size of said diagnostic image comprises switching between reversible compression and irreversible compression depending on whether said abnormal shadow candidate is detected or not, respectively.

3. A computer-aided image diagnosis system comprising:

means for detecting an abnormal shadow candidate in a radiation image, based on image information representing said radiation image;

means for switching a destination where a diagnostic image is output, in accordance with a result of the detection of said abnormal shadow candidate; and means for outputting said diagnostic image which corresponds to said detection result, wherein a first destination of the means for switching comprises a first display unit, wherein a second destination of the means for switching comprises a second display unit, wherein the second display unit has a higher quality than the first display unit.

4. The computer-aided image diagnosis system as set forth in claim 3, wherein said output means comprises a plurality of display units differing from one another in display quality; and wherein said means for switching a destination switches the radiation image to be output to at least one of said plurality of display units which displays said diagnostic image.

5. The computer-aided image diagnosis system as set forth in claim 3, wherein said output means comprises a plurality of display units differing from one another in display quality and a storage unit for storing said diagnostic image on a predetermined storage medium; and wherein said means for switching a destination switches the radiation image to be output to at least one of said plurality of display units which displays said diagnostic image, and also switches whether or not said diagnostic image is stored on said predetermined storage medium.

6. The system of claim 3 wherein the means for switching selects one of the first and second display units exclusive of the other for displaying said radiation image.

7. The system of claim 6 wherein said second display unit displays said radiation image compressed using reversible compression, and wherein said first display unit displays said radiation image compressed using irreversible compression.

* * * * *